US008573842B2

(12) United States Patent
Shao et al.

(10) Patent No.: US 8,573,842 B2
(45) Date of Patent: Nov. 5, 2013

(54) SENSOR CONTROL CIRCUIT AND SENSOR (75) Inventors: Zhenhua Shao, Torrance, CA (US); Christopher Lee Keller, Torrance, CA (US); Masataka Ito, Torrance, CA (US); Dongdong Wang, Torrance, CA (US)

(73) Assignee: Ibiden Co., Ltd., Ogaki-shi (JP)

( * ) Notice: Subject to any disclaimer, the term of this patent is extended or adjusted under 35 U.S.C. 154(b) by 321 days.

(21) Appl. No.: 13/012,322

(22) Filed: Jan. 24, 2011

(65) Prior Publication Data

US 2011/0234299 A1 Sep. 29, 2011

Related U.S. Application Data (60) Provisional application No. 61/318,088, filed on Mar. 26, 2010.

(51) Int. Cl.
*G01K 7/16* (2006.01)
*G01K 7/34* (2006.01)
*G01N 25/12* (2006.01)

(52) U.S. Cl.
USPC ............. 374/184; 374/170; 374/28; 374/143; 702/130; 73/73

(58) Field of Classification Search
USPC ............... 374/141, 16, 28, 170–173, 179, 374/183–185, 163, 143, 102; 702/130, 702/132–136; 73/73
See application file for complete search history.

(56) References Cited

U.S. PATENT DOCUMENTS

| | | | | |
|---|---|---|---|---|
| 3,488,529 A | * | 1/1970 | Howe | 327/512 |
| 4,324,138 A | * | 4/1982 | Davis et al. | 374/111 |
| 4,340,886 A | * | 7/1982 | Boldt et al. | 340/682 |
| 4,480,312 A | * | 10/1984 | Wingate | 702/130 |
| 4,503,707 A | * | 3/1985 | Rosa et al. | 374/142 |
| 4,563,682 A | * | 1/1986 | Merkel | 340/870.13 |
| 4,575,806 A | * | 3/1986 | Aldrich et al. | 702/133 |
| 4,751,495 A | * | 6/1988 | Whitman | 340/538.11 |
| 4,875,042 A | * | 10/1989 | Oku et al. | 340/870.17 |
| 5,105,366 A | * | 4/1992 | Beckey | 700/276 |
| 5,370,664 A | * | 12/1994 | Morgan et al. | 607/6 |
| 5,552,999 A | * | 9/1996 | Polgreen et al. | 702/63 |
| 5,927,854 A | * | 7/1999 | Kroll | 374/102 |
| 6,473,399 B1 | * | 10/2002 | Johansson et al. | 370/229 |

(Continued)

OTHER PUBLICATIONS

Analog Devices, Inc. Low Cost ±2g/10g Dual Axis iMEMS(R) Accelerometers with Digital Output, the United States, 1999. 11 pages.

*Primary Examiner* — Gail Verbitsky
(74) *Attorney, Agent, or Firm* — Oblon, Spivak, McClelland, Maier & Neustadt, L.L.P.

(57) ABSTRACT

A sensor control circuit for controlling a sensor unit for measuring a physical value includes a timing controller which selects periodically one or more sensor units among multiple sensor units and converts an output signal from the sensor unit to a continuous serial input signal, an oscillator which receives the serial input signal input by the controller and outputs a frequency signal corresponding to the output signal detected by the sensor unit, a counter which counts for a predetermined duration a number of pulses of the frequency signal output from the oscillator, a data converter which converts the number of pulses to voltage data and outputs the data, and an RLC selector which inputs to the converter information indicating a characteristic value on which the number of pulses is based. The characteristic value is resistance, inductance or electrostatic capacitance. The sensor units measure physical values, respectively.

16 Claims, 6 Drawing Sheets

(56) References Cited

U.S. PATENT DOCUMENTS

| | | | |
|---|---|---|---|
| 7,322,743 B2 * | 1/2008 | Gozloo et al. | 374/170 |
| 7,413,342 B2 * | 8/2008 | Mukherjee | 374/170 |
| 7,499,359 B2 * | 3/2009 | Choi et al. | 365/222 |
| 7,891,868 B2 * | 2/2011 | Sohn | 374/170 |
| 8,096,706 B2 * | 1/2012 | Lee | 374/170 |
| 8,354,875 B2 * | 1/2013 | Zhang et al. | 327/512 |
| 2005/0099163 A1 * | 5/2005 | Liepold | 320/150 |
| 2006/0195289 A1 * | 8/2006 | Choi et al. | 702/130 |
| 2007/0046300 A1 * | 3/2007 | Kay et al. | 324/725 |
| 2008/0049811 A1 * | 2/2008 | Hirano | 374/100 |
| 2008/0238650 A1 * | 10/2008 | Riihimaki et al. | 340/501 |
| 2009/0296779 A1 * | 12/2009 | Lee | 374/170 |
| 2011/0122917 A1 * | 5/2011 | Hamanaka et al. | 374/170 |
| 2012/0201273 A1 * | 8/2012 | Mukherjee | 374/183 |

\* cited by examiner

SENSOR CONTROL CIRCUIT AND SENSOR

CROSS-REFERENCE TO RELATED APPLICATIONS

The present application claims the benefits of priority to U.S. Application No. 61/318,088, filed Mar. 26, 2010. The contents of that application are incorporated herein by reference in their entirety.

BACKGROUND OF THE INVENTION

1. Field of the Invention

The present invention relates to a sensor control circuit and a sensor.

2. Discussion of the Background

Sensors such as acceleration, temperature, pressure and angle sensors to be used in a portable device are usually structured as modules in which a silicon MEMS sensor (MEMS: micro electro mechanical systems) and a control circuit, which outputs an input signal from such sensors as an output signal, are integrated and packaged (as for a MEMS sensor, see for example, an acceleration sensor described in Analog Devices, Inc. Low Cost ±2 g/10 g Dual Axis iMEMS (R) Accelerometers with Digital Output, the United States, 1999).

Figure 1:
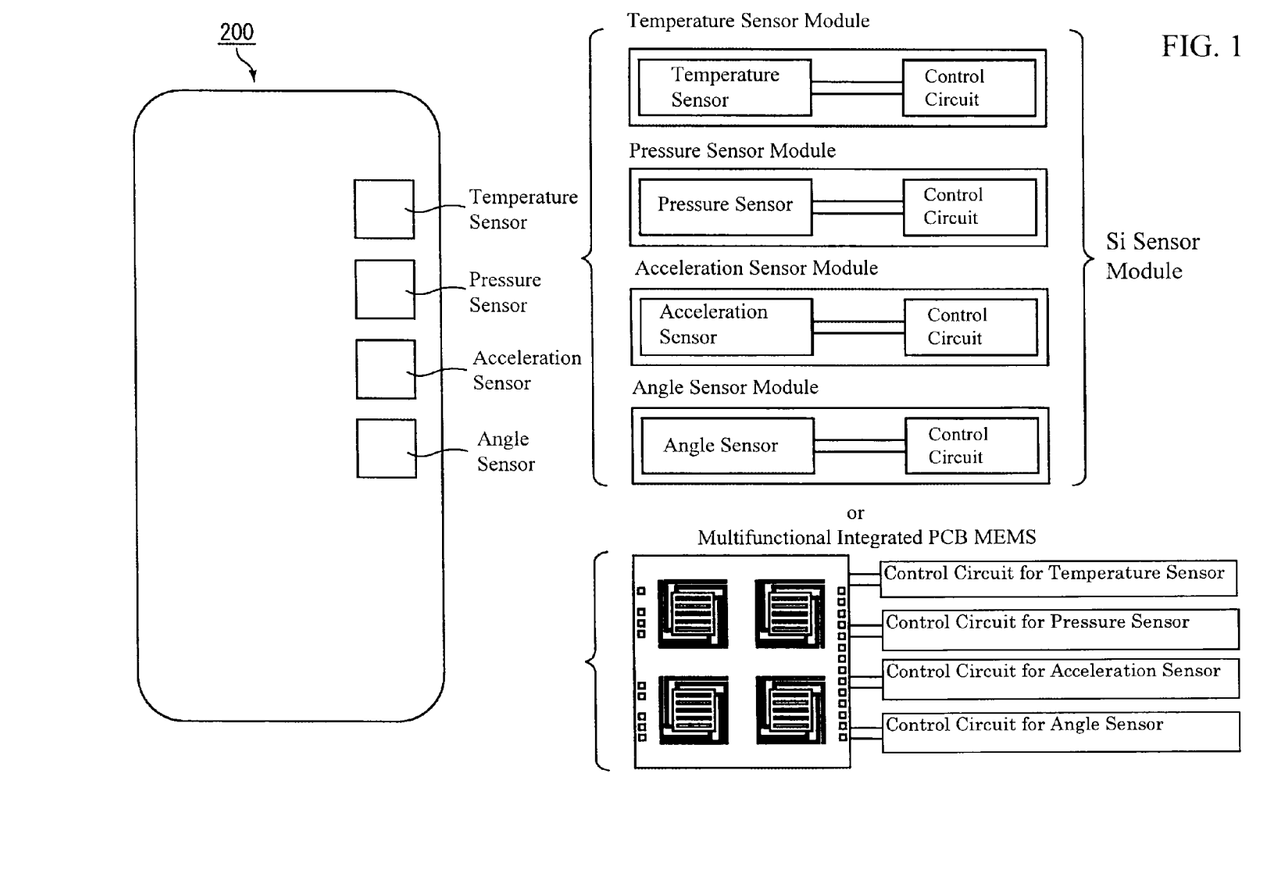
FIG. 1 is a view schematically showing an example where multiple types of sensors are arranged in a portable device.

FIG. 1 is a view schematically showing an example where multiple types of sensors are arranged in a portable device. FIG. 1 shows sensor 200 in which four sensors, a temperature sensor, a pressure sensor, an acceleration sensor and an angle sensor, are loaded in a portable device.

For allowing a portable device to measure multiple types of physical values by using the MEMS sensor described above, multiple types of sensor modules are required to be arranged separately. Top right of FIG. 1 shows an example where multiple types of sensor modules are arranged.

On the other hand, by integrating multiple types of sensors on a PCB (printed circuit board), systems such as multifunctional integrated PCB MEMS are suggested. When such a system is applied, decreased areas for mounting sensors themselves and reduced costs may be achieved. Bottom right of FIG. 1 is a schematic view showing an example of multi-functional integrated PCB MEMS and control circuits corresponding to their respective sensors.

The contents of this publication are incorporated herein by reference in their entirety.

SUMMARY OF THE INVENTION

According to one aspect of the present invention, a sensor control circuit for controlling a sensor unit for measuring a physical value includes a timing controller which selects periodically one or more sensor units among multiple sensor units and converts an output signal from the sensor unit to a continuous serial input signal, an oscillator which receives the continuous serial input signal input by the timing controller and outputs a frequency signal corresponding to the output signal detected by the sensor unit, a counter which counts for a predetermined duration a number of pulses of the frequency signal which is output from the oscillator, a data converter which converts the number of pulses to voltage data and outputs the voltage data, and an RLC selector which inputs to the data converter an information indicating a characteristic value on which the number of pulses counted by the counter is based. The characteristic value is one of resistance, inductance and electrostatic capacitance. The sensor units measure physical values, respectively.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

The embodiments will now be described with reference to the accompanying drawings, wherein like reference numerals designate corresponding or identical elements throughout the various drawings.

First Embodiment

In the following, a sensor control circuit and a sensor according to an embodiment of the present invention are described.

Figure 2:
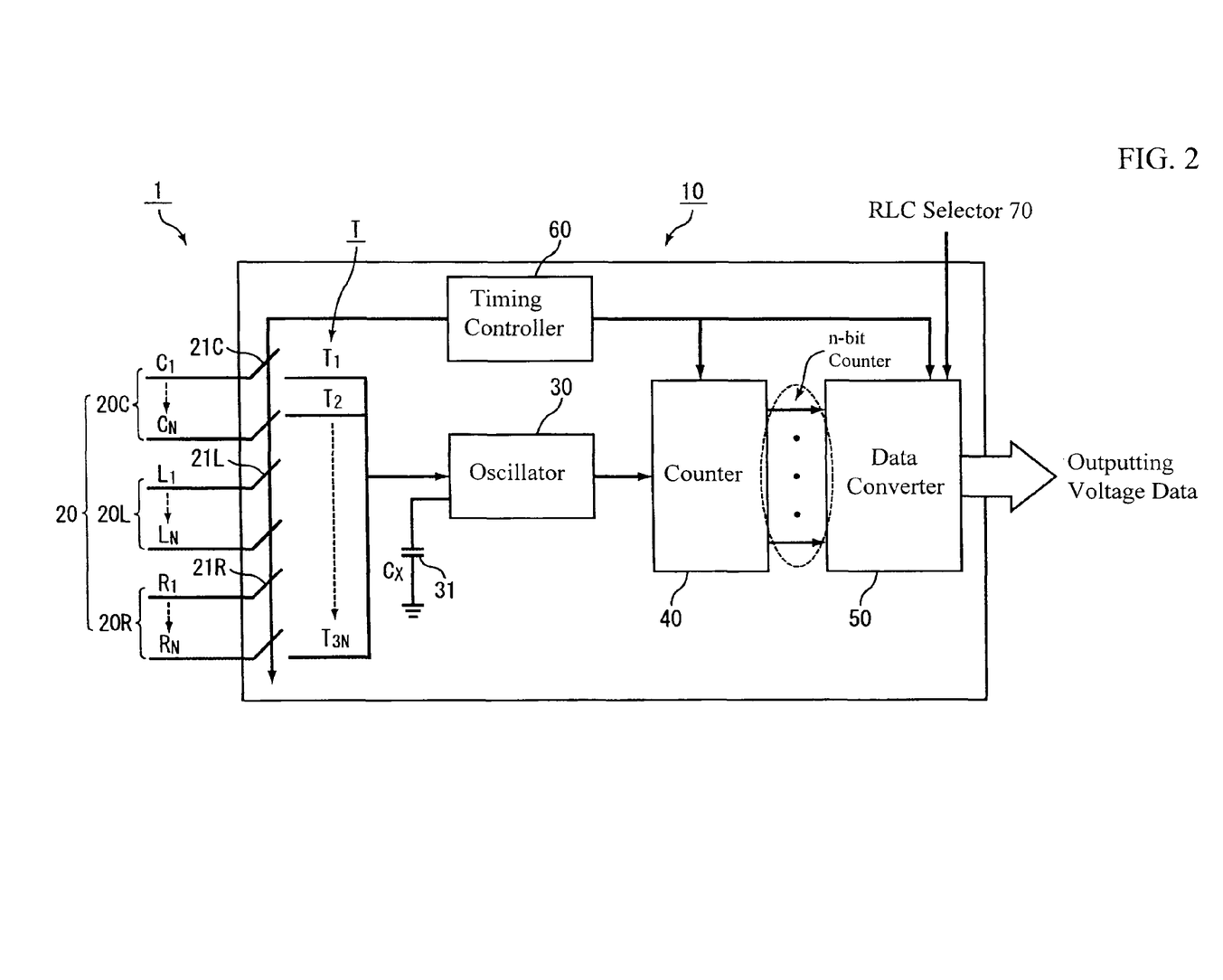
FIG. 2 is a block diagram schematically showing an example of the structure of a sensor control circuit and a sensor according to the present invention.

FIG. 2 is a block diagram schematically showing an example of the structure of a sensor control circuit and a sensor according to the present invention. Sensor control circuit 10 of the present embodiment shown in FIG. 2 has oscillator 30, counter 40, data converter 50, timing controller 60 and RLC selector 70. Sensor units 20 are positioned adjacent to sensor control circuit 10, and the end portions of sensor units 20 are electrically connected to sensor control circuit 10. Sensor 1 according to an embodiment of the present invention is structured with sensor control circuit 10 and sensor units 20.

Sensor units 20 connected to sensor control circuit 10 are described. Sensor units 20 are the following: sensor units (20C) for detecting an output signal indicating electrostatic capacitance as a characteristic value; sensor units (20L) for detecting an output signal indicating inductance as a characteristic value; and sensor units (20R) for detecting an output signal indicating resistance as a characteristic value. The number of sensor units (20C), (20L) and (20R) is not limited to any specific number. The number of respective sensor units (20C), (20L) and (20R) shown in FIG. 2 is "N" (N indicates any natural number).

As for sensor units (20C), components may be used in which electrostatic capacitance changes in response to a change in the physical value of a measurement object. In particular, sensor components with variable capacitors may be used. As for physical values to be measured in sensor units (20C), for example, humidity, pressure, acceleration or the like may be listed.

As for sensor units (20L), components may be used in which inductance changes in response to a change in the physical value of a measurement object. In particular, sensor components with variable coils may be used. As for physical values to be measured in sensor units (20L), for example, electric current or the like may be listed.

As for sensor units (20R), components may be used in which resistance changes in response to a change in the physical value of a measurement object. In particular, sensor components with variable resisters may be used. As for physical values to be measured in sensor units (20R), for example, temperature or the like may be listed.

At their respective end portions of sensor units 20, connection switches 21 (indicated as 21C, 21L and 21R) are formed. Corresponding to their respective connection switches, terminals T (indicated as $T_1$~$T_{3N}$) are formed to allow electrical connection and disconnection with connection switches 21. Switching between connection switches 21 and terminals T is conducted by later-described timing controller 60. Only one connection switch 21 and one terminal T are connected at one time. By switching connection switches 21 and terminals T, a sensor unit to be connected to the oscillator is selected. Namely, by switching connection switches 21 and terminals T, timing controller 60 converts a serial signal from a sensor unit 20 to a continuous serial input signal and inputs it to oscillator 30.

Each terminal T is electrically connected to oscillator 30. Oscillator 30 is an oscillation circuit where an oscillatory frequency is determined in response to a change in the characteristic value—electrostatic capacitance, inductance or resistance—which is detected at a sensor unit 20 connected to a terminal T. The oscillatory frequency output from oscillator 30 is input to later-described counter 40. Oscillator 30 is connected to ground through capacitor 31.

As described above, since only one each of connection switch 21 and terminal T are connected at a given time, if sensor unit (20C) and terminal T are connected, an oscillatory frequency is determined at oscillator 30 according to a change in the electrostatic capacitance detected at sensor unit (20C). Then, a frequency signal reflecting the electrostatic capacitance detected at sensor unit (20C) is output from oscillator 30. Even if inductance detected at sensor unit (20L) or resistance detected at sensor unit (20R) is changed while sensor unit (20C) and terminal T are connected, such a change in inductance or in resistance is not reflected in the frequency signal to be output from oscillator 30.

Also, when sensor unit (21L) and terminal T are connected, an oscillatory frequency is determined at oscillator 30 according to a change in the inductance detected at sensor unit (20L). Then, a frequency signal reflecting the inductance detected at sensor unit (20L) is output from oscillator 30. In the same manner, when sensor unit (21R) and terminal T are connected, an oscillatory frequency is determined at oscillator 30 according to a change in the resistance detected at sensor unit (20R). Then, a frequency signal reflecting the resistance detected at sensor unit (20R) is output from oscillator 30.

Figure 3:
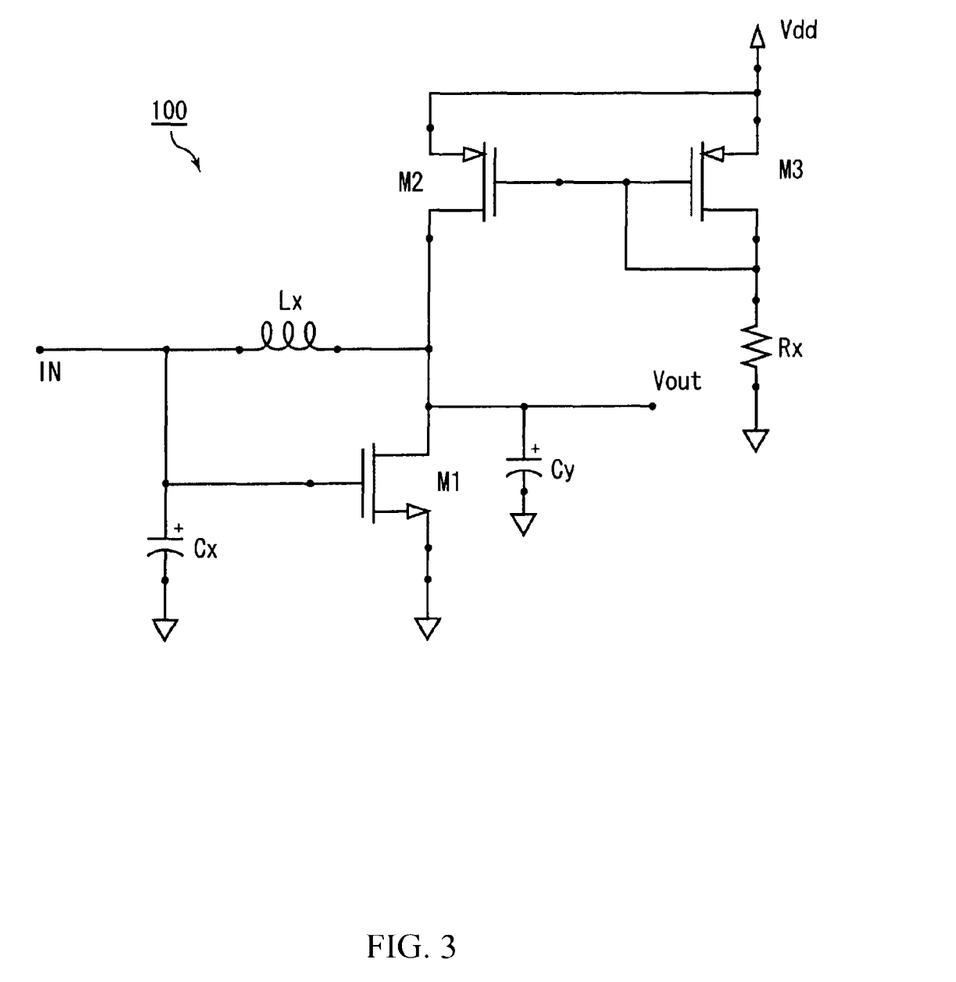
FIG. 3 is a circuit diagram showing an example of an oscillator.

As for the oscillator, oscillator circuit 100 as shown in FIG. 3 may be used, for example. However, the structure of an oscillator circuit is not limited to such a circuit. In oscillator circuit 100 shown in FIG. 3, the connection switch of a sensor unit is connected to "IN" in the drawing, and a frequency signal is output from "Vout."

The frequency signal output from the oscillator is input to counter 40. Counter 40 counts the number of pulses in a predetermined duration. Then, a signal corresponding to the number of pulses counted at counter 40 is input to data converter 50. Data converter 50 converts the number of pulses to voltage data and outputs the data.

Figure 4:
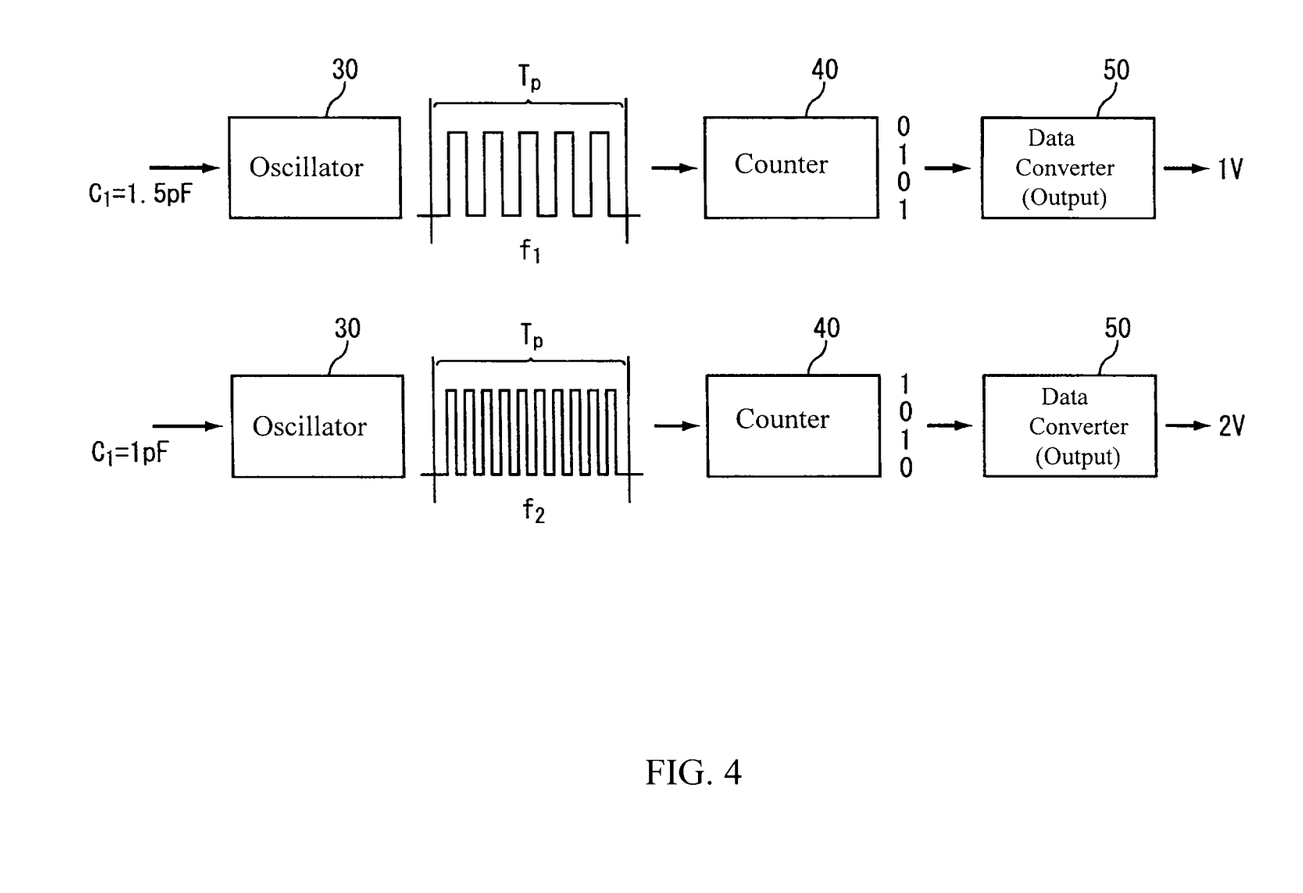
FIG. 4 is a view schematically illustrating a method to count at a counter the number of pulses of a frequency signal output from an oscillator and to convert the number of pulses to voltage data at a data converter and then to output the data.

FIG. 4 is a view schematically illustrating a method for counting at the counter the number of pulses of the frequency signal output from the oscillator, and for converting the number of pulses to voltage data at the data converter and then outputting the data.

In an example shown in the upper part of FIG. 4, sensor unit (20C) to detect electrostatic capacitance is connected to oscillator 30. In sensor unit (20C), electrostatic capacitance is detected as 1.5 pF, and corresponding to the electrostatic capacitance, frequency signal (f1) is output from oscillator 30. The number of pulses of frequency signal (f1) in predetermined duration (Tp) is 5. At counter 50, the number of pulses of frequency signal (f1) in predetermined duration (Tp) is counted and converted to a binary number, and a signal indicating the number of pulses is transmitted to data converter 60. At data converter 60, the input signal indicating the number of pulses is converted to voltage and the voltage is output. The voltage to be output in this example is 1V. Then, the physical value (acceleration) corresponding to the voltage is output as 1.2 G, for example.

In an example shown in the lower part of FIG. 4, electrostatic capacitance is detected as 1 pF in sensor unit (20C), and corresponding to the electrostatic capacitance, frequency signal (f2) is output from oscillator 30. The number of pulses of frequency signal (f2) in predetermined duration (Tp) is 10. The process at counter 50 to convert the number of pulses to a binary number and the process at data converter 60 to convert the signal to voltage are the same as in the example shown in the upper part of FIG. 4. The voltage to be output in this example is 2V. Then, the physical value (acceleration) corresponding to the voltage is output as 1.6 G, for example.

In examples shown in FIG. 4, sensor unit (20C) to detect electrostatic capacitance is connected to oscillator 30. In sensor control circuit 10 of the present embodiment shown in FIG. 2, sensor units to be connected to oscillator 30 are switched by timing controller 60. Timing controller 60 transmits a signal to connection switches 21 at a predetermined interval, and periodically switches connected points between connection switches 21 and terminals T. The mechanism for switching connected points is not limited to any specific type, and those such as follows may be used: a switching mechanism by inputting a signal transmitted from a timer circuit at a constant interval to a transistor; or a switch or relay which is turned ON/OFF by a signal transmitted from a timer circuit at a constant interval. In addition, to synchronize the timing of switching connected points with signal processing at counter 40 and data converter 50, signals are also transmitted to counter 40 and data converter 50 from timing controller 60.

In sensor 1, total (3N) sensor units indicated as ($C_1$-$C_N$), ($L_1$-$L_N$) and ($R_1$-$R_N$) are positioned adjacent to sensor control circuit 10. At sensor control circuit 10, total (3N) terminals indicated as ($T_1$-$T_{3N}$) are formed.

First, it is assumed that ($C_1$) and ($T_1$) are connected. At that time, other sensor units are not connected to terminals. Then, timing controller 60 is set to switch connected points every 1 millisecond, and the operation starts. For 1 millisecond while ($C_1$) and ($T_1$) are connected, an output signal indicating electrostatic capacitance is continuously input to oscillator 30 from ($C_1$). Based on the change in an output signal indicating electrostatic capacitance, an oscillatory frequency is determined at oscillator 30. Based on the oscillatory frequency output from oscillator 30, the number of pulses is counted, and voltage data based on the output signal indicating electrostatic capacitance detected at ($C_1$) is output for 1 millisecond.

Connected points are switched consecutively from the start of the operation; ($C_2$) and ($T_2$) are connected after 1 millisecond, ($C_3$) and ($T_3$) are connected after 2 milliseconds and so on. ($C_N$) and ($T_N$) are connected after (N−1) milliseconds from the start of the operation. Then, after N milliseconds from the start of the operation, ($L_1$) and ($T_{N+1}$) are connected. In the same manner, connected points continue to be switched until (3N−1) milliseconds have passed from the start of the operation. After (3N−1) milliseconds from the start of the operation, ($R_N$) and ($T_{3N}$) are connected. Then, after (3N) milliseconds from the start of the operation, ($C_1$) and ($T_1$) are connected again. In the following, switching the connected points is repeated in the same manner.

As the connected points are switched, the output signal (output signal detected at a sensor unit) to be input to oscillator 30 is changed and the value of the frequency signal to be output from oscillator 30 also changes. Then, voltage data, which are determined based on the frequency signal from oscillator 30 and are output, change as well. Namely, during 1~2 milliseconds after the start of the operation, voltage data based on the output signal indicating electrostatic capacitance detected at ($C_2$) are output. Then, in the same manner, during N~(N+1) milliseconds after the start of the operation, voltage data based on the output signal indicating inductance detected at ($L_1$) are output. Also, during (3N−1)~(3N) milliseconds after the start of the operation, voltage data based on the output signal indicating resistance detected at ($R_N$) are output. Then, during (3N)~(3N+1) milliseconds after the start of the operation, voltage data based on the output signal indicating electrostatic capacitance detected at ($C_1$) are output again.

Sensor control circuit 10 of the present embodiment further contains RLC selector 70. RLC selector 70 provides data converter 50 with data, indicating on which characteristic value—electrostatic capacitance, inductance or resistance—the result of measuring the number of pulses of a frequency signal output from oscillator 30 is based. In particular, synchronized with the switching of connected points by timing controller 60, RLC selector 70 provides data converter 50 with data, indicating on which characteristic value the number of pulses to be measured is based after the connected points are switched. Then, based on a signal indicating the number of pulses input from the counter and on a signal about the type of characteristic value input from RLC selector 70, data converter 50 determines the voltage to be output and then outputs the voltage. Also, based on the signal indicating the type of characteristic value input from RLC selector 70, the physical value to be output is determined, and the physical value to be displayed externally is also determined based on the output voltage.

The above description showed an example in which total (3N) sensor units are arranged to be connected to a sensor control circuit. Here, to simplify the description, an example is shown in which one each of sensor unit (20C), sensor unit (20L) and sensor unit (20R) are arranged. A timing chart is used to illustrate how voltage data are output from the sensor control circuit in such an example.

Figure 5:
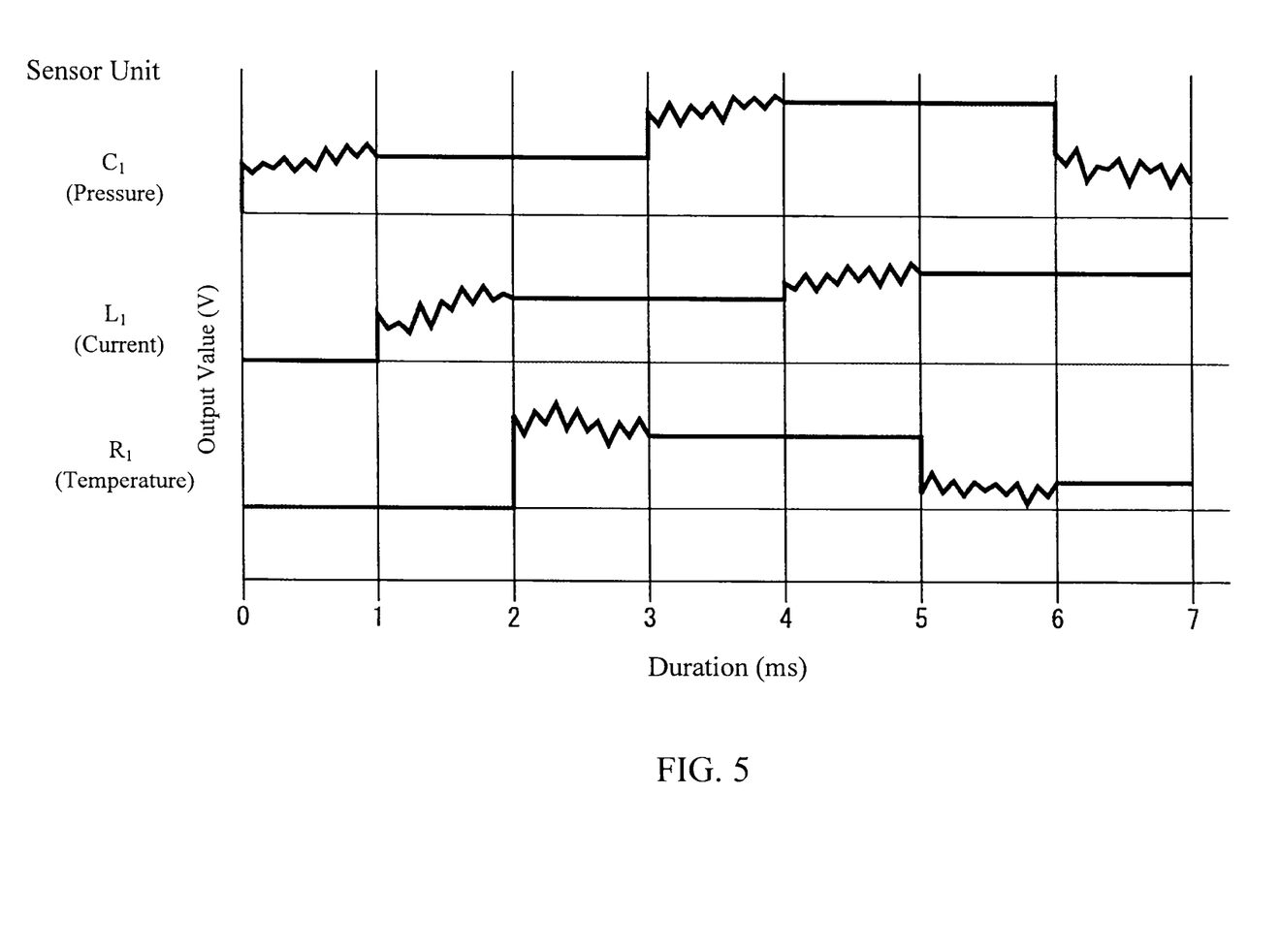
FIG. 5 is a timing chart showing an example of how voltage data are output from a sensor control circuit.

FIG. 5 is a timing chart showing an example of how voltage data are output from a sensor control circuit. Sensor unit ($C_1$) measures pressure as a physical value based on the change in electrostatic capacitance; sensor unit ($L_1$) measures electric current as a physical value based on the change in inductance; and sensor unit ($R_1$) measures temperature as a physical value based on the change in resistance. The timing chart shows how voltage data are output from the sensor control circuit when connected points are switched in the order of $C_1 \rightarrow L_1 \rightarrow R_1 \rightarrow C_1 \rightarrow \ldots$ every 1 millisecond.

During 0~1 millisecond from the start of the operation, voltage data are output for 1 millisecond based on the output signal indicating electrostatic capacitance detected at ($C_1$), and pressure value based on the voltage data is displayed externally. When 1 millisecond has passed after the start of the operation, the connected point is switched to ($L_1$). At that time, the voltage data carrying a pressure value retains the value when the connected points are switched. The pressure value displayed externally is also retained.

When 1 millisecond has passed after the start of the operation, and at the same time as the connected point is switched to ($L_1$), the RLC selector transmits a signal to the data converter, and the data converter recognizes that the subsequent signal indicating the number of pulses is based on the output signal detected at ($L_1$). During 1~2 milliseconds from the start of the operation, voltage data are output for 1 millisecond based on the output signal indicating inductance detected at ($L_1$), and an electric-current value based on the voltage data is displayed externally. When 2 milliseconds have passed after the start of the operation, the connected point is switched to ($R_1$). At that time, the voltage data carrying an electric-current value retain the value when the connected points are switched. The electric-current value displayed externally is also retained.

When 2 milliseconds have passed after the start of the operation, and at the same time as the connected point is switched to ($R_1$), the RLC selector transmits a signal to the data converter, and the data converter recognizes that the subsequent signal indicating the number of pulses is based on the output signal detected at ($R_1$). During 2~3 milliseconds from the start of the operation, voltage data are output for 1 millisecond based on the output signal indicating resistance detected at ($R_1$), and temperature based on the voltage data is displayed externally. When 3 milliseconds have passed after the start of the operation, the connected point is switched to ($C_1$) again. At that time, the voltage data carrying a temperature value retains the value when the connected points are switched. The temperature value displayed externally is also retained.

When 3 milliseconds have passed after the start of the operation, and as the connected point is switched to ($C_1$) again, a signal is simultaneously transmitted from the RLC selector to the data converter, and the data converter recognizes that the subsequent signal indicating the number of pulses is the signal based on the output signal detected at ($C_1$). Then, voltage data are output based on the value of the output signal indicating electrostatic capacitance detected at ($C_1$), but the output value shortly after the connected point is switched is discontinuous from the output value retained until then (the output value when 1 millisecond has passed after the start of the operation).

After that, connected points are switched every 1 millisecond, and electric-current value→temperature→pressure value→electric-current value→ . . . are repeatedly output in the same manner. Namely, in the sensor shown in the timing chart in FIG. 5, the duration when each physical value is actually measured is 1 millisecond among 3 milliseconds, and measured values of each physical value are not obtained for 2 milliseconds.

Namely, an outputting method of a sensor using the sensor control circuit of the present embodiment is different from that of a sensor, as shown in FIG. 1, which contains multiple types of sensor units and control circuits corresponding to their respective sensor units and which measures all physical values measured at each sensor unit as continuous values.

In a sensor using the sensor control circuit of the present embodiment, there is a duration in which no measured value is obtained for each physical value to be measured. However, a short duration of time when no measured value is obtained does not cause any problem as long as such a sensor is used for a purpose where change in a physical value for an extremely short duration is not a concern (for example, a temperature sensor, a humidity sensor or the like used in daily life). In addition, connected points are switched at every 1 millisecond in the above example. However, switching intervals are not limited specifically. By shortening switching intervals, substantially continuous values may be output.

Other Embodiments

In a sensor according to the present invention, sensor units are preferred to be arranged on a printed circuit board (PCB). Also, a sensor control circuit and sensor units are all preferred to be arranged on a printed circuit board. Such a printed circuit board is not limited to any specific type.

Figure 6:
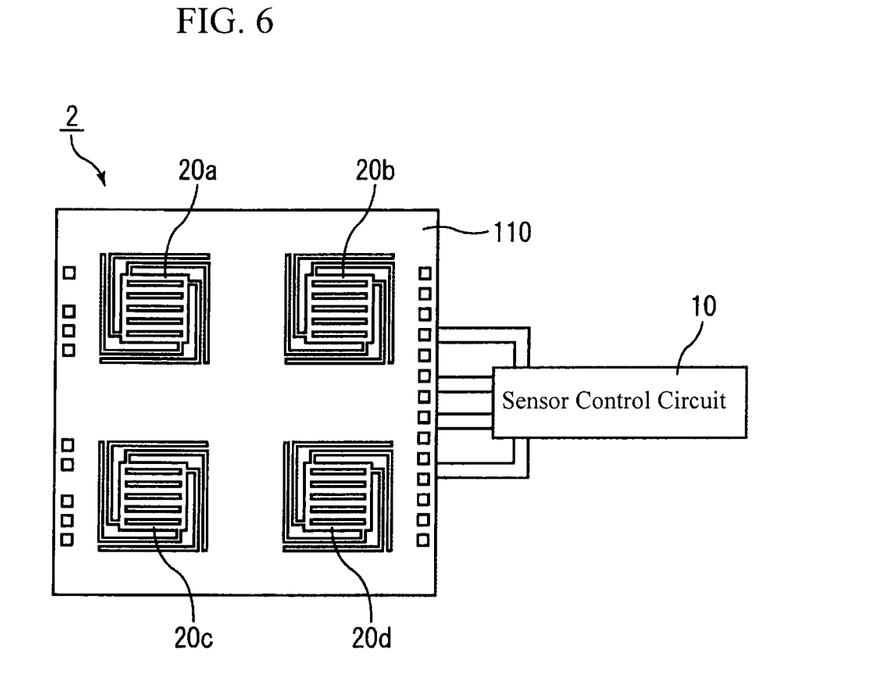
FIG. 6 is a plan view schematically showing an example of a sensor where sensor units are formed on a printed circuit board and a sensor control circuit is connected to the sensor units.

FIG. 6 is a plan view schematically showing an example of a sensor where sensor units are formed on a printed circuit board and a sensor control circuit is connected to the sensor units. Sensor 2 shown in FIG. 6 contains sensor control circuit 10 of the present invention, and temperature sensor unit (20a), pressure sensor unit (20b), acceleration sensor unit (20c) and angle sensor unit (20d) arranged on printed circuit board 110. Sensor control circuit 10 and each sensor unit 20 are electrically connected. Output signals detected at each sensor unit 20 are input to sensor control circuit 10, and voltage data corresponding to each output signal input to sensor control circuit 10 are output from sensor control circuit 10.

Figure 7:
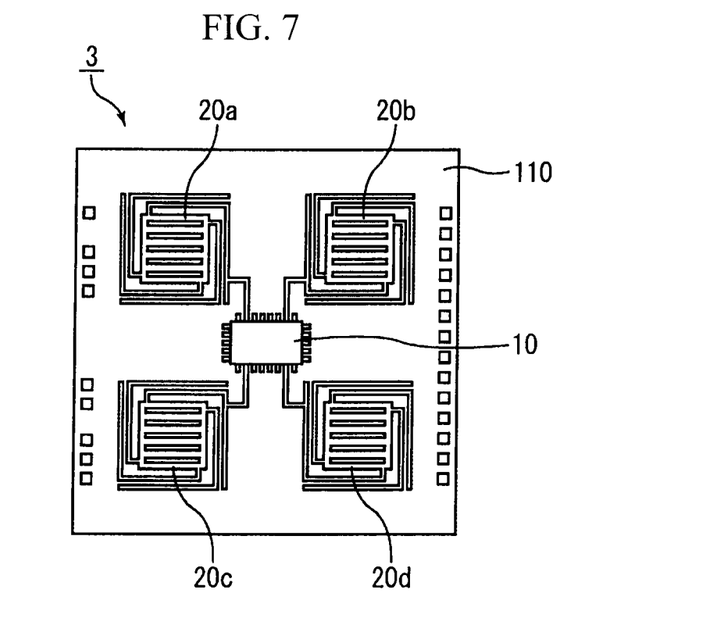
FIG. 7 is a plan view schematically showing an example of a sensor where sensor units are formed on a printed circuit board and a sensor control circuit is positioned on the printed circuit board and connected to the sensor units.

FIG. 7 is a plan view schematically showing an example of a sensor where sensor units are arranged on a printed circuit board, and a sensor control circuit is positioned on the printed circuit board and connected to the sensor units. In sensor 3 shown in FIG. 7, sensor unit (20a), pressure sensor unit (20b), acceleration sensor unit (20c) and angle sensor unit (20d) are formed on printed circuit board 110, and sensor control circuit 10 is further positioned (mounted) on printed circuit board 110. Then, sensor control circuit 10 and each sensor unit 20 are electrically connected. Output signals detected at each sensor unit are input to sensor control circuit 10, and voltage data corresponding to each output signal input to sensor control circuit 10 are output from sensor control circuit 10.

It is sufficient if a sensor control circuit of the present invention sets any characteristic value from among resistance, inductance and electrostatic capacitance as a detection object. It is not required for one sensor control circuit to set three types of characteristic values—resistance, inductance and electrostatic capacitance—as detection objects. For example, only resistance may be set as a detection object. Alternatively, only two types of characteristic values such as resistance and inductance may be set as detection objects.

A sensor control circuit of the present invention may also be used as a sensor to which one sensor unit is connected. Essentially, since selection of a sensor unit by a timing controller is not conducted in such a sensor, it may be used as a sensor to measure a physical value continuously.

A sensor control circuit according to an embodiment of the present invention is suitable for being loaded in a portable device, whose mounting area is small, and which can process input signals from sensor units by using a single control circuit and then output them as output signals. Also, a sensor according to an embodiment of the present invention contains such a control circuit.

Namely, a sensor control circuit is such a sensor control circuit that it is connected to single or multiple sensor units for measuring a physical value by detecting an output signal carrying any characteristic value of resistance, inductance or electrostatic capacitance. Such a sensor control circuit has the following: an oscillator to output a frequency signal corresponding to an output signal detected at a sensor unit; a timing controller to select periodically a sensor unit from among the sensor units so as to be connected to the oscillator, to convert the output signal from the sensor unit to a continuous serial input signal, and to input it to the oscillator; a counter to count for a predetermined duration the number of pulses of the frequency signal which is output from the oscillator; a data converter to convert the number of pulses to voltage data and to output the data; and an RLC selector to input information to the data converter to indicate on which characteristic value— resistance, inductance or electrostatic capacitance—the number of pulses counted at the counter is based.

The sensor control circuit is connected to a sensor unit for detecting an output signal which carries any characteristic value of resistance, inductance or electrostatic capacitance. The characteristic value detected in the sensor unit is input to an oscillator in the sensor control circuit, and a frequency signal is output from the oscillator. Then, the number of pulses of the frequency signal, which is output from the oscillator, is counted at a counter, and the number of pulses is converted to voltage data at a data converter, which are then output.

Also, the sensor control circuit contains a timing controller, which periodically selects a sensor unit to be connected to the oscillator and converts an output signal from the sensor unit to a continuous serial input signal, which is then input to the oscillator. Therefore, only the output signal detected at a sensor unit, which is connected to the oscillator by the timing controller, is input to the oscillator as a continuous serial input signal.

If a sensor control circuit has such a mechanism an output signal, which carries any characteristic value of resistance, inductance or electrostatic capacitance is input to an oscillator. Then, such an output signal passes through the oscillator, the counter and the data converter and is output as voltage data, corresponding to the output signal which was input to the oscillator.

Since a sensor unit to be connected to the oscillator is periodically selected by the timing controller, after a sensor unit is selected by the timing controller, an output signal carrying any characteristic value of resistance, inductance or electrostatic capacitance detected by the selected sensor unit, is input to the oscillator. Then, such a signal passes through the oscillator, the counter and the data converter, and is output as voltage data, corresponding to the output signal which was input to the oscillator.

The sensor control circuit further contains an RLC selector, which inputs information to the data converter to indicate on which characteristic value—resistance, inductance or electrostatic capacitance—the number of pulses counted at the counter is based. In response as the timing controller periodically selects a sensor unit to be connected to the oscillator, the RLC selector inputs information to the data converter to indicate on which characteristic value—R (resistance), L (inductance) or C (electrostatic capacitance)—the frequency signal to be input to the counter is based. Then, based on the information, output voltage and the type and the value of a physical value to be output are determined in the data converter.

Namely, if an RLC selector is loaded, regardless of the output signal which is input to an oscillator and which carries any characteristic value of resistance, inductance or electrostatic capacitance, a proper output value may be obtained.

Namely, in the sensor control circuit, although control circuits for their respective sensor units are not loaded, voltage data may be obtained, corresponding to an output signal carrying any of the characteristic values from among resistance, inductance and electrostatic capacitance detected by a sensor unit.

The sensor control circuit may be connected to at least two sensor units for detecting output signals carrying at least any two characteristic values from among resistance, inductance and electrostatic capacitance. A conventional sensor control circuit can process only one characteristic value—resistance, inductance or electrostatic capacitance. Therefore, if a sensor unit detects output signals that carry at least two characteristic values from among resistance, inductance and electrostatic capacitance, at least two control circuits are required to be loaded.

On the other hand, in the sensor control circuit, when an output signal is detected in a sensor unit carrying any of the characteristic values from among resistance, inductance and electrostatic capacitance, such an output signal carrying the detected characteristic value is input in the same oscillator. Since a sensor unit to be connected to the oscillator is periodically selected by the timing controller, output signals carrying two or more characteristic values from among resistance, inductance and electrostatic capacitance are not input to the oscillator at the same time. At any given time, only an output signal from the sensor unit connected to the oscillator at that time is input to the oscillator. Then, a frequency signal corresponding to the output signal, which was input to the oscillator, is output from the oscillator. Then, the signal passes through the counter and the data converter, and voltage data are obtained. Accordingly, a sensor control circuit may be constructed by using one control circuit to process output signals carrying at least two characteristic values from among resistance, inductance and electrostatic capacitance, In the sensor control circuit, the physical value to be measured by the above resistance may be temperature. Also, in the sensor control circuit, the physical value to be measured by the above inductance may be electric current. In the sensor control circuit, the physical value to be measured by the above electrostatic capacitance may be at least one type selected from among a group of humidity, pressure and acceleration.

The sensor may be characterized by having the sensor control circuit described above and sensor units which are formed on a printed circuit board or in a printed circuit board and are connected to the sensor control circuit.

The sensor may be characterized by the following: the sensor control circuit described above is positioned on a printed circuit board, and sensor units connected to the sensor control circuit are formed on the printed circuit board or in the printed circuit board. If sensor units are formed on a printed circuit board or in a printed circuit board, multiple types of sensor units may be simultaneously loaded using resin material in the printed circuit board without going through a semiconductor process. Thus, sensor units may be prepared at lower cost. In addition, if a sensor control circuit is arranged on a printed circuit board, a smaller-size sensor may be obtained.

Obviously, numerous modifications and variations of the present invention are possible in light of the above teachings. It is therefore to be understood that within the scope of the appended claims, the invention may be practiced otherwise than as specifically described herein.

What is claimed is:

1. A sensor control circuit for controlling a sensor unit for measuring a physical value, comprising:
    a timing controller configured to select periodically at least one sensor unit among a plurality of sensor units and convert an output signal from the sensor unit to a continuous serial input signal;
    an oscillator configured to receive the continuous serial input signal input by the timing controller and output a frequency signal corresponding to the output signal detected by the sensor unit;
    a counter configured to count for a predetermined duration a number of pulses of the frequency signal which is output from the oscillator;
    a data converter configured to convert the number of pulses to voltage data and output the voltage data; and
    an RLC selector configured to input to the data converter an information indicating a characteristic value on which the number of pulses counted by the counter is based,
    wherein the characteristic value is one of resistance, inductance and electrostatic capacitance, the plurality of sensor units are configured to measure a plurality of physical values, respectively, and the timing controller is configured to transmit a signal to connection switches of the sensor units at a predetermined interval such that the at least one sensor unit is selected periodically among the plurality of sensor units.

2. The sensor control circuit according to claim 1, wherein the timing controller is configured to select periodically at least two sensor units among the plurality of sensor units and convert two output signals carrying two characteristic values, respectively.

3. The sensor control circuit according to claim 1, wherein the characteristic value is resistance, and the sensor unit is configured to measure temperature as the physical value.

4. The sensor control circuit according to claim 1, wherein the characteristic value is inductance, and the sensor unit is configured to measure electric current as the physical value.

5. The sensor control circuit according to claim 1, wherein the characteristic value is electrostatic capacitance, and the sensor unit is configured to measure at least one of humidity, pressure and acceleration as the physical value.

6. A sensor, comprising:
    a sensor control circuit according to claim 1; and
    a sensor unit connected to the sensor control circuit and configured to be formed on or in a printed circuit board.

7. A sensor according to claim 6, wherein the sensor control circuit is positioned on a printed circuit board, and the sensor unit connected to the sensor control circuit is formed on or in the printed circuit board.

8. The sensor control circuit according to claim 1, further comprising a plurality of terminals positioned to be electrically connected or disconnected with the connection switches of the sensor units at connected points, respectively, wherein the timing controller is configured to transmit the signal to the connection switches such that the connected points are periodically switched between connection and disconnection.

9. The sensor control circuit according to claim 8, wherein the timing controller is configured to transmit signals to the counter and the data converter such that timing of switching the connected points is synchronized with signal processing at the counter and the data converter.

10. The sensor control circuit according to claim 9, wherein the RLC selector is configured to provide the information to the data converter in synchronization with the switching of the connected points.

11. A sensor, comprising:
   sensor control circuit according to claim 10; and
   a sensor unit connected to the sensor control circuit and configured to be formed on or in a printed circuit board.

12. A sensor according to claim 11, wherein the sensor control circuit is positioned on a printed circuit board, and the sensor unit connected to the sensor control circuit is formed on or in the printed circuit board.

13. The sensor control circuit according to claim 1, wherein the timing controller is configured to transmit the signal to the connection switches such that the sensor control circuit is electrically connected to one of the sensor units at one time.

14. The sensor control circuit according to claim 13, further comprising a plurality of terminals positioned to be electrically connected or disconnected with the connection switches of the sensor units, respectively, wherein the timing controller is configured to transmit the signal to the connection switches such that one of the connection switches is electrically connected to one of the terminals at one time.

15. A sensor, comprising:
   sensor control circuit according to claim 14; and
   a sensor unit connected to the sensor control circuit and configured to be formed on or in a printed circuit board.

16. A sensor according to claim 15, wherein the sensor control circuit is positioned on a printed circuit board, and the sensor unit connected to the sensor control circuit is formed on or in the printed circuit board.

* * * * *